Figure 1:
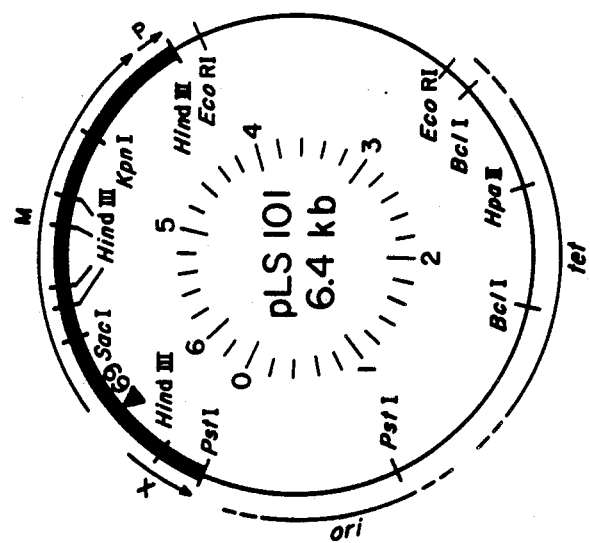
Figure 1:
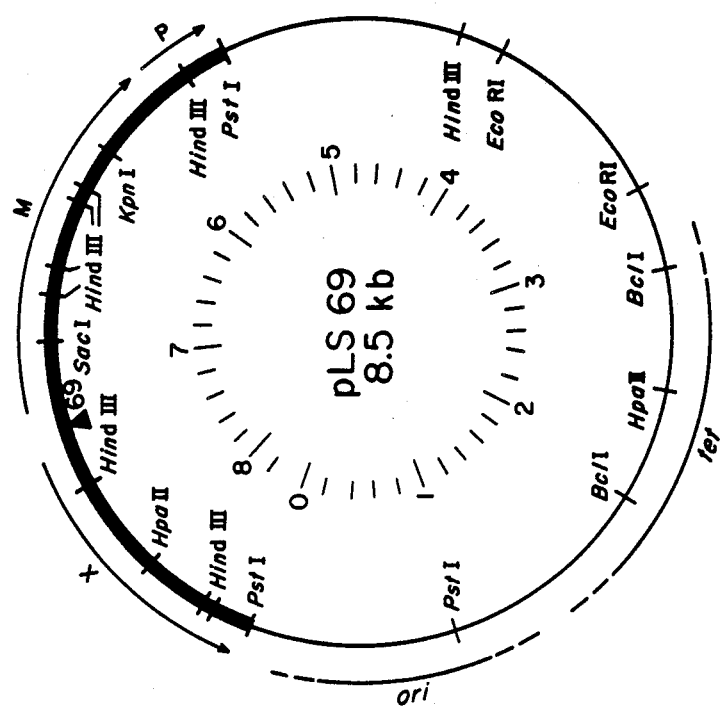

United States Patent [19]
Lacks et al.

[11] Patent Number: 4,729,954
[45] Date of Patent: Mar. 8, 1988

[54] PLS010 PLASMID VECTOR

[75] Inventors: Sanford A. Lacks, Brookhaven; Tanjore S. Balganesh, Upton, both of N.Y.

[73] Assignee: The United States of America as represented by the United States Department of Energy, Washington, D.C.

[21] Appl. No.: 702,766

[22] Filed: Feb. 19, 1985

[51] Int. Cl.$^4$ .................... C12N 15/00; C12N 1/00
[52] U.S. Cl. .................... 435/172.3; 435/320; 935/29; 935/22
[58] Field of Search ............ 435/317, 172.3, 91; 935/22, 27, 29

[56] References Cited
U.S. PATENT DOCUMENTS

| | | | |
|---|---|---|---|
| 4,332,898 | 6/1982 | Reusser | 435/172.3 |
| 4,362,816 | 12/1982 | Reusser | 435/172.3 |
| 4,393,137 | 7/1983 | Manis et al. | 435/172.3 |

OTHER PUBLICATIONS

Stassi et al., Proc. Natl. Acad. Sci., 78:7028–7032 (1981).
Stassi et al., Genetics Exchange, edited by Stoeiks et al., Marcel Dekker, Inc. pp. 235–246 (1982).
Locks et al., Cell 31:327–336 (1982).
Locks, Genetics 53:207–235 (1966).
Lopez et al., J. Bacterial, 150:692–701 (1982).
Ghei et al., J. Bacterial, 93:816–829 (1967).
Marcina et al., J. Bacterial, 143:1425–1435 (1980).
Currier et al., Aval. Biochem. 76:431–441 1976.

Primary Examiner—Alvin E. Tanenholtz
Attorney, Agent, or Firm—Margaret C. Bogosian; James W. Weinberger; Judson R. Hightower

[57] ABSTRACT

Disclosed is recombinant plasmid pLS101, consisting essentially of a 2.0 Kb malM gene fragment ligated to a 4.4 Kb T$_c$r DNA fragment, which is particularly useful for transforming Gram-positive bacteria. This plasmid contains at least four restriction sites suitable for inserting exogeneous gene sequences. Also disclosed is a method for plasmid isolation by penicillin selection, as well as processes for enrichment of recombinant plasmids in Gram-positive bacterial systems.

3 Claims, 5 Drawing Figures

BEFORE ENRICHMENT

AFTER ENRICHMENT

PLS010 PLASMID VECTOR

The U.S. Government has rights in this invention pursuant to Contract Number DE-AC02-76CH00016, between the U.S. Department of Energy and Associated Universities Inc.

UTILITY STATEMENT

Molecular cloning in Gram-positive bacteria is particularly suited for the production of proteins because the absence of an outer membrane allows secretion of the product directly into the medium. The plasmid of this invention contains at least six different restriction sites into which DNA fragments can be inserted for cloning. The process using this plasmid provides a new method of recombinant plasmid isolation (by penicillin selection), as well as processes for enrichment of recombinant plasmids in highly transformable Gram-positive bacterial systems.

STATEMENT OF DEPOSIT

The plasmids of this invention have been deposited in the American Type Culture Collection in accordance with the Manual of Patent Examining Procedure and prior to the filing of this application. This deposit assures permanence and availability of the plasmid for at least the life of the patent. Plasmid pLS101 has been accorded ATCC deposit number 39938. Plasmid pLS69 has been accorded ATCC deposit number 39937.

SUMMARY OF THE INVENTION

Plasmid pLS101 was constructed for use as a vector for molecular cloning in Gram-positive bacteria such as *Streptococcus pneumoniae, Bacillus subtilis,* and other bacterial strains such as *E. coli.* The plasmid contains two selectable genes, tet and malM, each of which contains two or more restriction sites for insertion of DNA fragments to be cloned. Two selectable markers, Tc$^r$ and Mal+, can be exploited for the cloning of DNA fragments produced by a variety of restriction enzymes. Furthermore, insertional inactivation of the malM gene (specifically, either Tc$^r$ or Mal+) allows direct selection by penicillin treatment of cells with recombinant plasmids as TcRMal− transformants.

The strategy for the enrichment of recombinant plasmids for cloning in *S. pneumoniae* depends on the nature of the DNA fragments to be cloned. Thus, for the cloning of homogeneous DNA fragments from plasmids or viruses, insertion into a vector treated with alkaline phosphatase efficiently enriches for recombinants. Such fragments may be either homologous or heterologous with respect to the recipient chromosome. The technique of enrichment for recombinant plasmids by chromosomal facilitation is used for cloning heterogeneous DNA, such as chromosomal fragments from *S. pneumoniae* itself, that are homologous to the recipient chromosome. For dealing with DNA both heterogeneous and heterologous, that is, foreign DNA in general, enrichment is obtained by insertion into sites within the mal gene of pLS101. Only recombinant-containing clones, which are unable to use maltose, survive the penicillin selection treatment.

In addition to enrichment of recombinant plasmids, the technique of chromosomal facilitation offers another advantage for cloning pneumococcal genes. It eliminates the contribution of independent chromosomal transformation by chromosomal marker DNA fragments in the ligation mixture used for the initial transformation. Such transformation coupled with independent vector establishment gives spurious recombinant clones, in which the desired chromosomal marker is not in fact located in the plasmid. In the enrichment transformation the transforming activity of the residual chromosomal DNA for that particular marker is negligible, so that transformed clones carrying both plasmid and chromosomal markers almost always contain the desired recombinant plasmid.

BACKGROUND OF THE INVENTION

The mechanism of genetic recombination in transformation is the replacement of a single strand sequence in the recipient chromosome by the corresponding sequence of a single strand of donor DNA. The physical association of donor DNA with the recipient genome is paralleled by the appearance of recombinant DNA that carries both donor and recipient genetic markers (Ghei et al., *J. Bacteriol,* 93, 816–829, 1967). However, entry of transforming DNA into a recipient cell does not ensure transformation; the transforming DNA must be integrated with the host cell's DNA. Early discoveries by Lacks and Hotchkiss (*Biochem. Biopys. ACTA,* 39, 508–517, 1960) found that cells in different mutant cultures bind to or allow entry of the same amount of wild type DNA, but these cells exhibit different degrees of genetic transformation. Steps subsequent to the binding and entry of transforming DNA, culminating in the integration into the host genome, are important in establishing the degree of transformation; this depends on the individual mutation and marker effects. Physiological conditions, defined as the "competence" of the bacterial cell to undergo transformation, control the cell's ability to bind and allow entry of transforming DNA. The proportion of competent cells can be calculated by genetic analysis—by comparing the frequency observed for double transformation of the unlinked markers (or mutation sites) with the frequency predicted from the product of single transformation frequencies.

In molecular cloning it is desirable to enrich for recombinant plasmids with respect to the regenerated vector in the transformed cell population. For cloning in *Escherichia coli* the treatment of a linearized vector with alkaline phosphatase is commonly used for such enrichment. Exploration of this approach in *S. pneumoniae* showed that it was unsuitable for cloning fragments present in heterogeneous mixtures of chromosomal DNA on account of the fate of DNA during entry into cells of transformable Gram-positive species. However, the phosphatase method was applicable for the cloning of homogeneous DNA fragments that are derived, for example, from plasmids or viruses.

A novel method for enrichment of recombinant plasmids containing inserts homologous to the host chromosome is described in the Specific Disclosure. This method is based on the phenomenon of chromosomal facilitation of plasmid establishment (Lopez, et al., *J. Bacteriol.,* 150, 692–701, 1982). Inasmuch as plasmids with homology to the chromosome are transferred at least ten times more frequently than vectors lacking homology, an additional passage of the plasmid population through the host will enrich for recombinants by a similar factor. Although demonstrated here in *S. pneumoniae,* this method applies to other Gram-positive bacteria, such as *Bacillus subtilis,* as well.

The study of alkaline phosphatase treatment of the vector is illuminating in several respects. In the process of binding and uptake of transforming DNA in *S. pneumoniae* and *B. subtilis*, the donor DNA is converted to single-stranded DNA fragments within the cell. The failure of hemiligated recombinant plasmids—generated by the ligation of an alkaline phosphatase treated vector with heterogeneous DNA fragments—to be established can be attributed to this process. Because of the similarity of their uptake mechanisms to *S. pneumoniae*, alkaline phosphatase treatment has limited value for cloning in other species of Streptococcus or Bacillus. Construction of recombinant plasmids using a phosphatase treated vector in *Streptococcus sanguis* has been reported for plasmid fragments, but not for chromosomal DNA (Macrina, et al., *J. Bacteriol.*, 143, 1425–1435, 1980). Inasmuch as alkaline phosphatase treatment of vector is an efficient technique for enrichment of recombinant plasmids in *E. coli*, it appears that DNA molecules entering the *E. coli* cell remain intact and double stranded.

The ability of recombinant hemiligated plasmids with heterogeneous inserts to become established in a particular transformable species for which the structure of DNA molecules entering the cell is not known is useful as a diagnostic tool to determine whether the DNA gaining entry has been converted to single-stranded fragments.

FIGURE LEGENDS

FIG. 1. Maps of *S. pneumoniae* plasmids pLS69 and pLS101. The heavy line represents the mal insert; the light line, the vector pMV158, or in the case of pLS101, a portion thereof.

Figure 2:
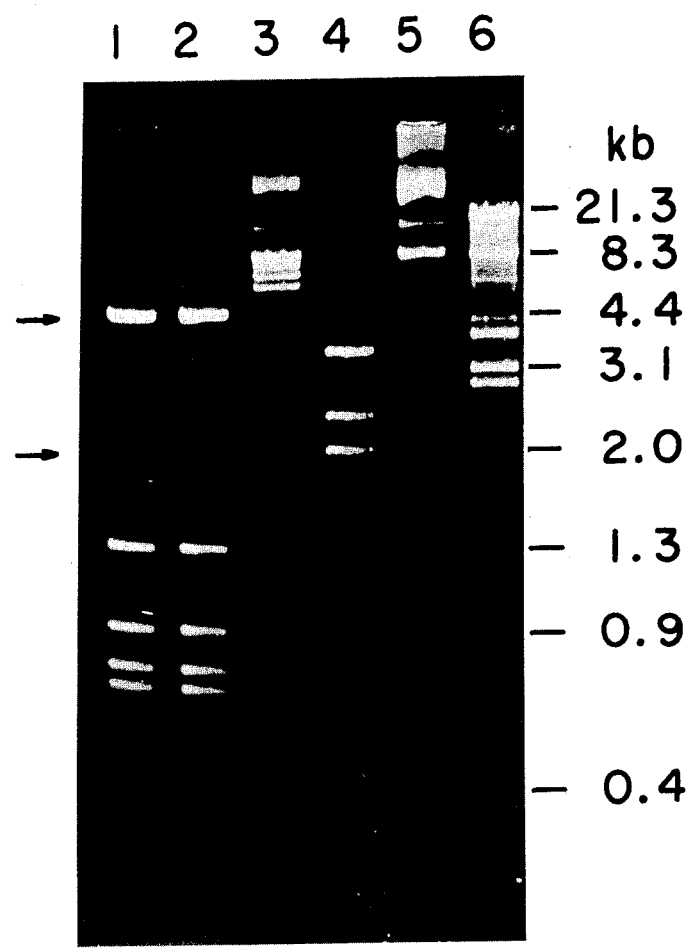

FIG. 2. Digestion of pLS69 with various concentrations of HindIII. Lanes 2, 3, 3 and 5 show restriction pattern obtained with 5.0, 0.5, 0.05 and 0.005 U/ml, respectively. Lane 4, pLS70, and Lane 6, T7 DNA cut with DpnII, provide reference fragments. The arrows indicate the 2.0-kb and 4.4-kb fragments that were isolated from parallel lanes and ligated together to produce pLS100 and pLS101.

Figure 3:
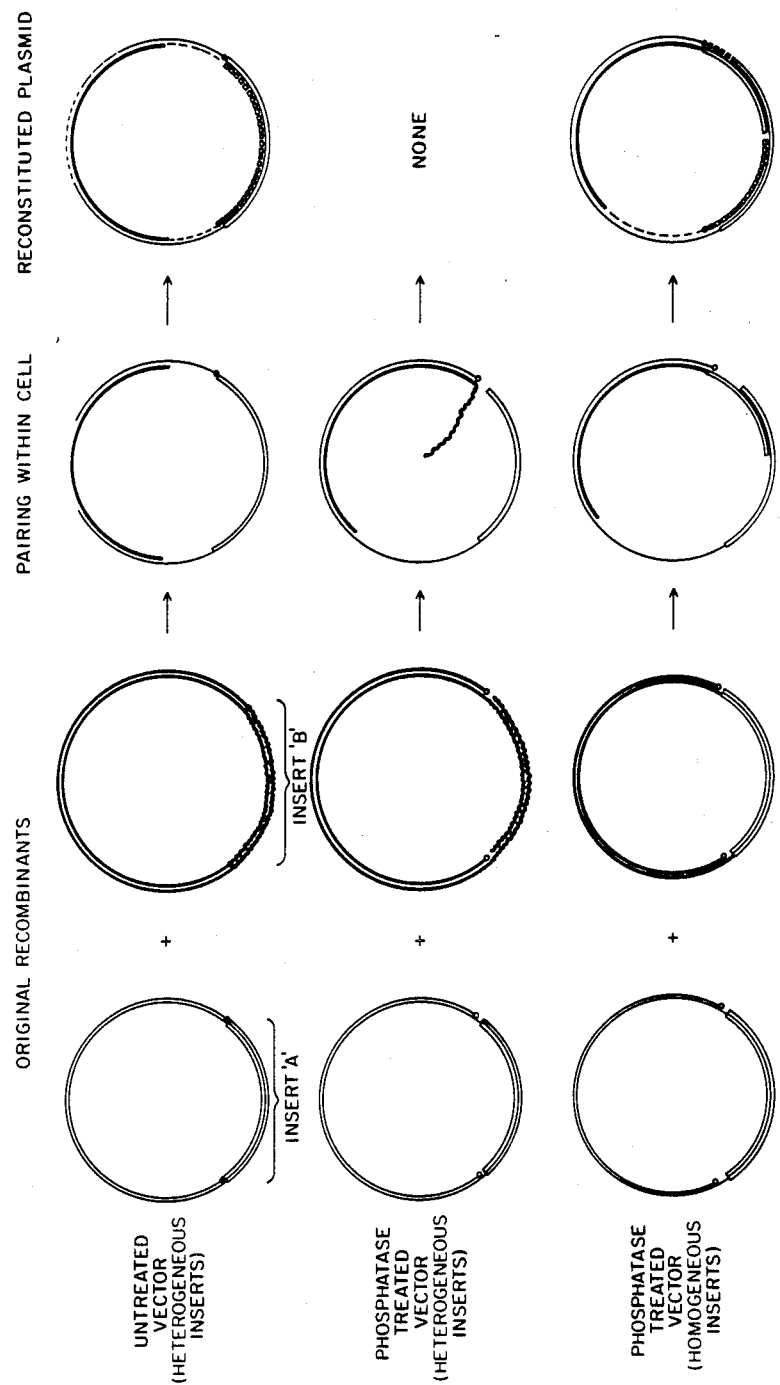

FIG. 3. Effect of removal of vector terminal phosphates on recombinant plasmid reconstitution. The light and heavy lines represent the vector portions of recombinant plasmids that separately enter a cell. Original recombinants depict the structures of plasmid molecules in the ligation mixture. Note nicks at joints of recombinants formed with phosphatase treated vectors. The interaction of two single-stranded plasmid fragments within the cell is shown. In the reconstituted plasmid broken lines represent newly synthesized DNA.

FIG. 4. Recovery of recombinant plasmids in cloning of total chromosomal fragments before and after enrichment by facilitation. BclI digested chromosomal DNA was ligated to BclI cut pLS101. A. Sampling of plasmids obtained in the initial transformation. B. Sampling of plasmids in the second transformation, except Lane 6, which contains pLS101 alone. Crude extracts were subjected to electrophoresis in 1% agarose gels, stained with ethidium bromide and photographed under UV. The lowest band in each lane corresponds to covalently closed monomers. The arrows indicate monomer forms of plasmid pLS101 and the shortened plasmid resulting from loss of the BclI-B fragment. In A, Lane 9, the plasmid was degraded to open circular and linear forms. In B, Lanes 2 and 4, the bands below the native monomeric forms of the recombinant plasmids may represent alkali denatured forms.

Figure 5A:
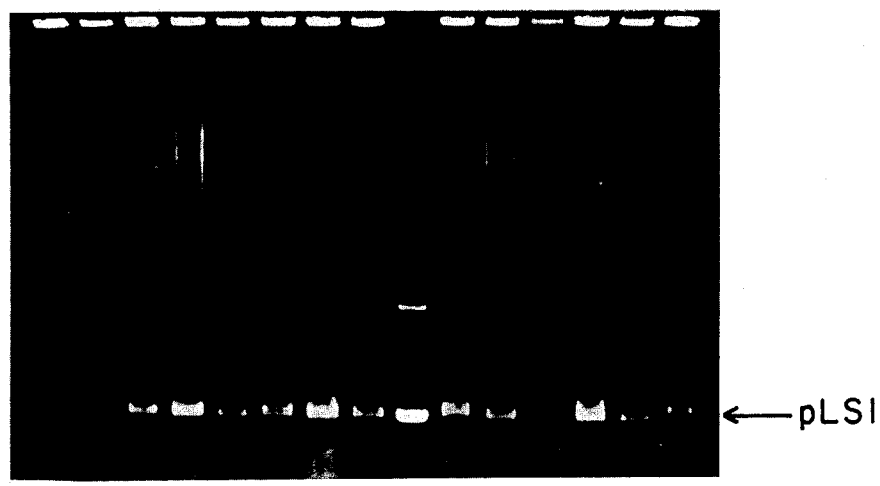
Figure 5B:
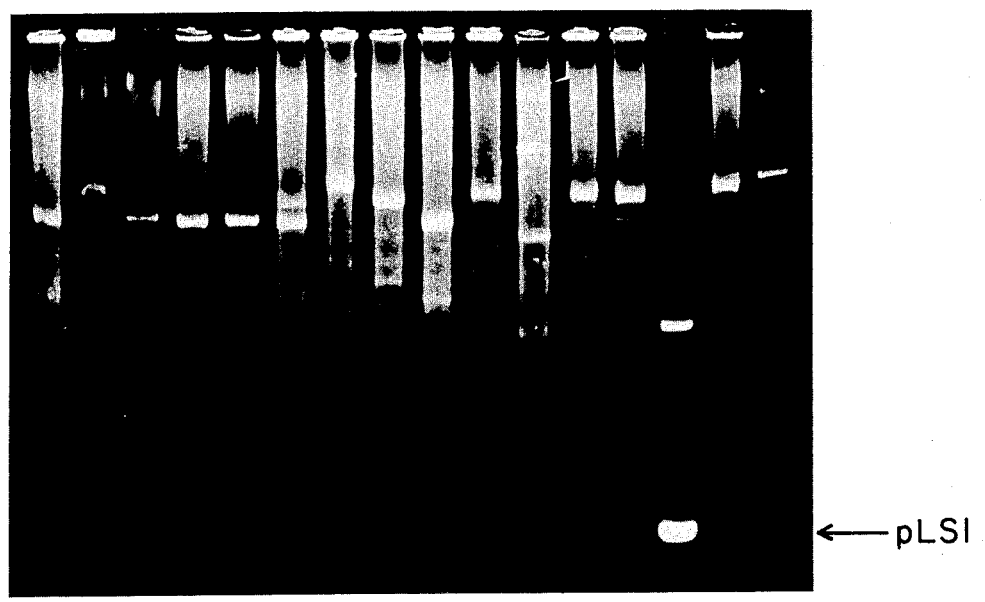

FIG. 5. Effect of chromosomal facilitation in cloning fragments of defined size. Chromosomal DNA was cut with EcoRI site of pLS1. Recombinant plasmids recovered: A. After the initial transformation; B. After enrichment and a second transformation, except Lane 14, which contains pLS1 alone. Crude extracts were analyzed in 1% agarose gels. Arrows indicate the position of the monomeric form of pLS1. A single recombinant plasmid was recovered in A (Lane 1). Alkali denatured forms are visible as diffuse bands below the monomeric forms of the recombinant plasmids in B.

SPECIFIC DISCLOSURE

(a) Bacterial strains and transformation

The strains of *S. pneumoniae* used are derived from R6. Strains 193 and 767 each carries the mal deletion 581, and 175 has the point mutation 567 in the amylomaltase gene of the chromosome. Cultures are grown at 37° C. to $10^8$ CFU/ml, diluted 20-fold and incubated at 30° C. for 30 min. DNA is then added generally at a concentration of 0.1 to 0.5 ug/ml, and the cultures are incubated at 30° C. for 40 min. Cultures are further incubated at 37° C. for 2 hours before plating on selective media. For the selection of Mal+ transformants, 0.2% maltose is substituted for sucrose in the medium. Tc$^r$ transformants are selected at a Tc concentration of 1.0 ug/ml. The pLS69 vector is described in Lacks, et al., Cell, 31, 327–336, 1982.

(b) Plasmid purification, restriction enzyme analysis, and ligation pLS101 is derived from pLS69, a derivative plasmid that differs from pLS70 by a 0.4 Kb deletion in the interior of the chromosomal insert. pLS69 exhibits only 1/10 the amylomaltase activity of pLS70; the deletion in pLS69 thus behaves as a down promoter mutation that reduces transcription to 1/10th its normal rate.

Purified plasmids were prepared by the method of Currier, et al. (*Anal. Biochem.*, 76, 431–441, 1976). Generally, reaction mixtures contain 10 mM Tris HCl (pH 7.4), 10 mM $MgCl_2$, 10 mM beta-mercaptoethanol and 50 mM NaCl. With EcoRI, Tris HCl is raised to 100 mM and beta-mercaptoethanol was omitted. To obtain both complete and partial digests of pLS69, various amounts of HindIII were added to samples of the plasmid and incubated at 30° C. for 16 h. Aliquots are analyzed by electrophoresis on a 1% agarose gel, and appropriate sized fragments are identified under UV after ethidium bromide staining. Gel segments containing these fragments are cut from unstained parallel lanes, macerated, and eluted in 0.5 ml of 10 mMTris HCl, 0.1 mM EDTA, pH8, for 20 h at 4° C. After sedimentation of the agarose, the DNA in the supernatant fluid is precipitated with ethanol and dissolved in 10 ul of the same buffer.

Crude plasmid extracts are prepared by modifying the method of Birnboim and Doly (Stassi, et al., *Genetic Exchange*, Streips, et al. ed., Marcel Dekker, New York, pp 235–246, 1982). Generally, cultures of 1.5 ml grown to an $OD_{650}$ of 0.6 are lysed with 0.1% sodium deoxycholate for 5 min at 37° C., after which 0.175N and NaOH and 1.0% $NaDodSo_4$ are added. The final DNA precipitate is dissolved in 10 ul of 10 mM Tris HCl, 0.1 mM EDTA, pH 8.0, and analyzed on 1% agarose gels. To prepare plasmid DNA for the second transformation in recombinant enrichment experiments, the initially transformed culture is diluted 30-fold into selective media. Crude plasmid extracts are then made from 30 ml of these cultures grown to $OD_{650}$ of 0.6.

Ligation mixtures contained 10 ug of DNA in 10 ul of 30 mM Tris HCl, pH 7.6, 10 mM MgCl$_2$. The procedure of Stassi, et al. (Stassi, et al., *PNAS*, 78, 7028-7032, 1981) was followed for ligation.

(c) Penicillin selection of Mal$^-$ cells

The procedure of Lacks (Lacks, *Genetics*, 53, 207-235, 1966) was followed. Generally, cells transformed to Tc$^r$ by DNA in the ligation mixture are grown in medium containing Tc at 1.0 ug/ml until the culture reached an OD$_{650}$ of 0.3. The culture is centrifuged and the cells are washed and transferred into maltose medium containing penicillin at 0.2 U/ml. After incubation at 37° C. for 16 h, surviving cells are sedimented and plated on maltose medium with limiting amounts of sucrose to allow identification of the Mal$^-$ clones as small colonies.

(d) Alkaline phosphatase treatment

Calf intestinal alkaline phosphatase is purified on Sephadex G75; the enzyme at a concentration of 25 U/ml is used in a total reaction mixture of 10 ul containing 1.2 ug of DNA. Incubation was carried out at 37° C. for 40 min, followed by 20 min at 65° C. The DNA is then purified by phenol extraction, ethanol precipitation, and dialysis.

Preparation of pLS101

1. These are 8 HindIII sites on the cloned fragment in pLS69 (FIG. 1). Samples of pLS69 were digested with various concentrations of HindIIi and the fragments were separated by agarose gel electrophoresis (FIG. 2). A 2.0-kb fragment, which harbors the entire coding sequence of the malM gene, was isolated from a partially digested sample (Lane 3) and ligated to the 4.4-kb fragment obtained by complete digestion (Lane 1). The latter fragment contains the region coding for Tc$^r$ as well as the plasmid origin of replication. The ligation mixture was used to transform *S. pneumoniae* strain 193. All four Mal+ transformants obtained were also Tc$^r$ and carried 6.4-kb plasmids. Analysis by restriction enzymes showed two plasmids to have the 2.0-kb fragment ligated to the 4.4-kb fragment in the same orientation as they are in pLS69; these plasmids were called pLS101 (FIG. 1). The other plasmids, which contain the fragments in opposite orientation, were called pLS100. The unique restriction sites for KpnI and SacI on the malM gene can be used for cloning DNA fragments. The recombinants among the Tc$^r$ transformants are Mal$^-$ by virtue of the insertional inactivation of the malM gene. They can be enriched by penicillin selection of Mal$^-$ cells (Lacks, 1966). This approach was tested by ligating a KpnI digest of chromosomal DNA from *S. pneumoniae* with KpnI linearized pLS101. The ligated mixture was used to transform cells of strain 193, in which the chromosomal mal region is deleted. Tc$^r$ transformants were grown up in medium containing Tc and subjected to penicillin selection. Twelve Mal$^-$ isolates were examined for the presence of recombinant plasmids. All of them appeared to harbor plasmids larger than pLS101, with the size of the insert varying from approximately 0.1 kb to 20 kb.

EXAMPLES

Example 1

The HpaII site on pLS101 can also be used for cloning (see Table I, below), and the Mal+ transformants can be screened for recombinants by checking for Tc sensitivity because insertions into the HpaII site inactivate the tet gene. The HpaII site could also by used for cloning DNA fragments generated by TaqI, AcyI, ClaI and AsuII digestion. Another useful cloning site is produced on removal of the smaller BclI fragment of pLS101. The larger fragment retains plasmid functions other than Tc$^r$, and DNA fragments generated by BclI, BamHI, BglII or DpnII can be cloned into its BclI site (see Table II, below). Similarly, EcoRI digestion of pLS101 removes the dispensable EcoRI fragment, generating an EcoRI site that can be used for cloning.

Example 2

The effect of phosphatase treatment of the vector pLS101, linearized with HpaII, on the establishment of recombinant plasmids containing HpaII fragments of total *S. pneumoniae* chromosomal DNA was examined. When a ligation mixture containing the phosphatase treated vector was used to transform *S. pneumoniae* cells, a very low frequency of plasmid establishment was observed (Table I). The frequency was less than 0.1% of that obtained in the control experiment using HpaII linearized pLS101 that had not been treated with phosphatase. Inasmuch as the proportion of recombinants in the control experiment was 25%, these results show that the phosphatase treatment eliminated the transfer of recombinant plasmids, as well as the religation and transfer of vector plasmids. Furthermore, no enrichment of recombinants was obtained. The majority of plasmid transfer in the control experiment resulted from religation of the vector. This was understandably eliminated by phosphatase treatment, but ligation of phosphate treated vector to untreated chromosomal DNA fragments could proceed to give recombinant plasmids. However, these recombinants failed to become established in the recipient cells. This presumably resulted from the hemiligated condition of these recombinant plasmids. An explanation of the inability of hemiligated recombinant plasmids to become established is presented in FIG. 3. The topmost array in FIG. 3 represents the probable pathway for establishment of a recombinant plasmid in *S. pneumoniae*. When total chromosomal DNA is digested with a restriction enzyme, a heterogeneous population of DNA fragments is formed. Therefore on ligation to a linearized vector, the completely ligated recombinant plasmid molecules that are generated carry DNA inserts that are generally different from one plasmid to another. The transforming DNA molecule in *S. pneumoniae* is processed so that only single stranded segments of DNA enter the cell. Hence, for the establishment of a functional replicon, the entering single strand of a recombinant plasmid must interact with a complementary single stranded DNA segment, which generally comes from the vector region, that contains overlapping regions of homology.

EXAMPLE 3

The ligation of a chromosomal DNA digest to a linearized and phosphatase treated vector results in the generation of hemiligated recombinant plasmid molecules (FIG. 3, middle array). Because the chromosomal DNA fragments were heterogeneous, the recombinant molecules generally contain different inserts. However, the pre-existing nicks in the hemiligated molecule result in the disruption of any recombinant strand entering the cell at one junction of the insert and vector. This would be in addition to other breaks produced during DNA uptake. Restoration of the junction between insert and vector would necessitate synapsis with a complementary fragment overlapping this site. The heterogeneous nature of the inserts makes it unlikely that another recombinant plasmid with the same insert would enter the cell to provide the complementary fragment for such an overlap. Thus, heterogeneous hemiligated recombinant plasmids fail to become established.

Example 4

In contrast, hemiligated recombinant molecules carrying homogeneous insert DNA should be able to establish themselves because two fragments that are complementary at the junction regions are likely to enter the same cell (FIG. 3, lowest array). To examine this, SV40 DNA was linearized with HpaII and ligated to phosphatase treated pLS101 which had also been linearized with HpaII. On transforming strain 193 with this ligation mixture, $3.2 \times 10^2$ Mal+ transformants were obtained. This was approximately 5% of the frequency of Mal+ transformants obtained in a control experiment using HpaII linearized SV40 DNA ligated to pLS101 not treated with phosphatase. The frequency among the Mal+ transformants of plasmids carrying inserted SV40 DNA was 93% when the phosphatase treated vector was used, as against 23% when the untreated vector was used (Table I).

Example 5

The frequency of plasmid establishment in *S. pneumoniae* was shown to be increased tenfold if the plasmid carried a DNA insert homologous to the recipient chromosome (Lopez, et al., 1982). The higher transfer efficiency of recombinant plasmids was investigated as a possible method for enrichment of recombinants.

Figure 4A:
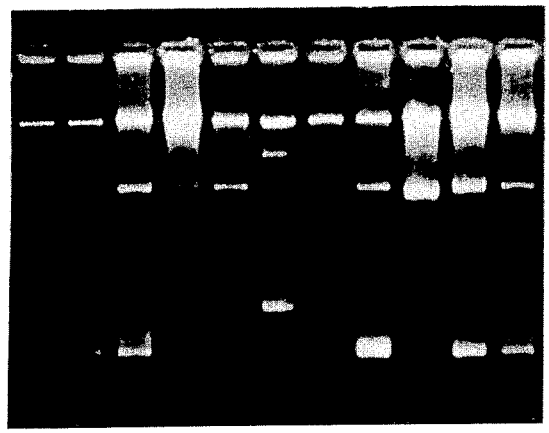
Figure 4B:
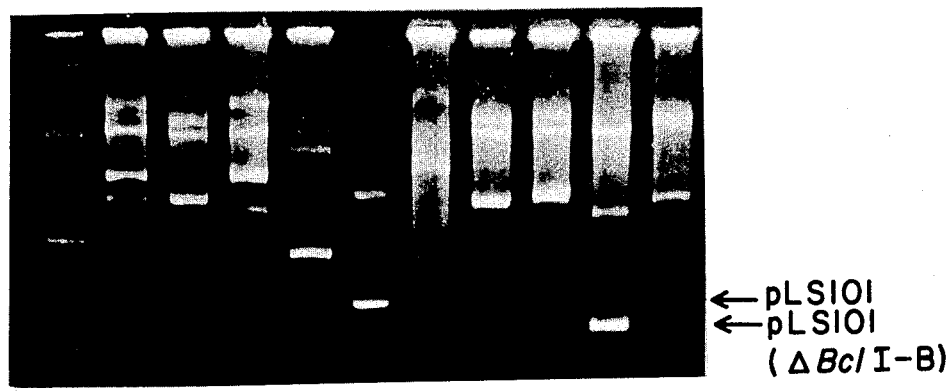

Cells of *S. pneumoniae* strain 767 were transformed with a ligation mixture containing total chromosomal DNA and pLS101 both digested with BclI. On screening 10 of the Mal+ transformants for plasmid size, no recombinant plasmids were detected (Table II, initial transformation; FIG. 4A). The transformed culture was then diluted into medium containing maltose, grown up, and a total plasmid extract was made. This plasmid extract was then used to transform *S. pneumoniae* 767 cells. Of the 10 Mal+ transformants analyzed, 9 carried insert DNA of various sizes (FIG. 4B), demonstrating the enrichment expected for facilitated establishment of recombinant plasmids. A similar enrichment that gave a 90% yield of recombinant plasmids was obtained by the same technique when BamHI cleaved chromosomal DNA was ligated to pLS101 cut with BclI (Table II).

Enrichment of recombinant clones by facilitation was also successful with fractionated chromosomal DNA (Table II). An EcoRI digested DNA fraction containing fragments 8 to 12 kb in size was ligated to the EcoRI cut pLS1. In this case the initially transformed culture was grown up in Tc, and Tc$^r$ transformants were selected in the second round. All of the transformants examined contained recombinant plasmids varying slightly in size with inserts apparently within the expected range of 8 to 12 kb (FIG. 5).

TABLE I

Effect of Treatment with Alkaline Phosphatase on Vector and Recombinant Plasmid Transfer

| Source of inserted DNA[a] | Phosphatase treatment of vector | Mal+ transformants per ml[b] | Proportion of recombinants[c] |
|---|---|---|---|
| S. pneumoniae | − | $1.01 \times 10^4$ | 2/8 |
| S. pneumoniae | + | 10 | 0/1 |
| SV 40 | − | $6.65 \times 10^3$ | 3/13 |
| SV 40 | + | $3.20 \times 10^2$ | 13/14 |

[a]Vector pLS101 and inserted DNA were cut with HpaII.
[b]Transformation recipient was *S. pneumoniae* strain 193.
[c]Ratio of the number of transformant clones with plasmids larger than pLS101 to the total tested.

TABLE II

Enrichment of Recombinant Plasmids by Facilitation

| | Donor DNA | | | Initial transformation[a] | | | Enrichment transformation[b] | | |
|---|---|---|---|---|---|---|---|---|---|
| Recipient strain | Vector | Vector site | Chromosomal fragments | Marker selected | Transformants per ml | Proportion of recombinants[c] | Marker selected | Transformants per ml | Proportion of recombinants[c] |
| 767 | pLS101 | BclI | BclI | Mal+ | $3.6 \times 10^4$ | 0/10 | Mal+ | $1.3 \times 10^4$ | 9/10 |
| 767 | pLS101 | BclI | BamHI | Mal+ | $3.5 \times 10^3$ | 4/10 | Mal+ | $4.2 \times 10^4$ | 9/10 |
| 767 | None | — | Uncut[d] | Str$^r$ | $2.3 \times 10^4$ | — | — | — | — |
| 175 | pLS1 | EcoRI | EcoRI | Tc$^r$ | $4.4 \times 10^4$ | 2/19 | Tc$^r$ | $1.1 \times 10^4$ | 15/15 |
| 175 | None | — | Uncut[d] | Str$^r$ | $7.8 \times 10^5$ | — | — | — | — |

[a]Transformation of recipient cells with the original ligation mixture.
[b]Transformation of recipient cells with a crude plasmid extract made from initially transformed cells grown up in selective medium.
[c]The ratio of transformants showing plasmids larger than the vector to the total number tested.
[d]Uncut chromosomal DNA with str$^r$ as reference marker was used to assay competence of recipient culture.

What is claimed is:

1. Recombinant plasmid pLS101, deposited in the American Type Culture Collection under deposit #39938, which is characterized as a Mal+ transformant and consists essentially of a 2.0 Kb MalM gene fragment ligated to a 4.4 Kb Tc$^r$ DNA fragment and inserted in a suitable Gram-positive bacteria.

2. A method of producing recombinant plasmid pLS101 consisting essentially of
digesting plasmid pLS69 into fragments;
removing by electrophoresis a first fragment containing a 2.0 Kb and malM gene sequence;
removing by electrophoresis a second fragment containing a 4.4 Kb Tc$^r$ DNA sequence;
ligating said first fragment to said second fragment to form a ligation product;
transforming a suitable Gram-positive bacteria with said ligation product.

3. The process of claim 2 wherein a second transforming step enriches the recombinant plasmid vector obtained, said step consists of removing said recombinant plasmid from the transformed cell population to form a plasmid extract; suitable bacterial cells are then transformed by said plasmid extract, and analyzed for the existence of Mal+ sequences indicating the presence of a recombinant plasmid in the transformed cell.

* * * * *